(12) United States Patent
Ozero

(10) Patent No.: US 11,932,615 B2
(45) Date of Patent: Mar. 19, 2024

(54) METHOD FOR RECOVERY OF ETHYLENE OXIDE

(71) Applicant: Brian Ozero, Westhampton Beach, NY (US)

(72) Inventor: Brian Ozero, Westhampton Beach, NY (US)

(*) Notice: Subject to any disclaimer, the term of this patent is extended or adjusted under 35 U.S.C. 154(b) by 700 days.

(21) Appl. No.: 17/059,556

(22) PCT Filed: May 14, 2019

(86) PCT No.: PCT/US2019/032179
§ 371 (c)(1),
(2) Date: Nov. 30, 2020

(87) PCT Pub. No.: WO2019/236249
PCT Pub. Date: Dec. 12, 2019

(65) Prior Publication Data
US 2021/0163434 A1    Jun. 3, 2021

Related U.S. Application Data

(60) Provisional application No. 62/680,210, filed on Jun. 4, 2018.

(51) Int. Cl.
C07D 301/32 (2006.01)
B01D 1/30 (2006.01)
B01D 3/38 (2006.01)
B01D 53/14 (2006.01)

(52) U.S. Cl.
CPC ............ *C07D 301/32* (2013.01); *B01D 1/305* (2013.01); *B01D 3/38* (2013.01); *B01D 53/1406* (2013.01); *B01D 53/1418* (2013.01); *B01D 53/1487* (2013.01); *B01D 53/1493* (2013.01); *B01D 2252/103* (2013.01)

(58) Field of Classification Search
CPC .................................................. C07D 301/32
See application file for complete search history.

(56) References Cited

U.S. PATENT DOCUMENTS

| 3,964,980 A | 6/1976 | Ozero |
| 4,134,797 A | 1/1979 | Ozero |
| 8,129,551 B2 | 3/2012 | Szul et al. |
| 2009/0216032 A1* | 8/2009 | Ozero .................. C07C 29/106 549/523 |
| 2010/0029962 A1 | 2/2010 | Szul et al. |
| 2010/0278711 A1 | 11/2010 | Find |

OTHER PUBLICATIONS

ISR for International Application PCT/US2019/032179.
Written Opinion for International Application PCT/US2019/032179.

* cited by examiner

*Primary Examiner* — Paul V Ward
(74) *Attorney, Agent, or Firm* — LADAS & PARRY LLP

(57) ABSTRACT

Ethylene oxide purification by quenching and washing ethylene oxide reactor effluent prior to passing the gaseous ethylene oxide-containing stream to an ethylene oxide absorber to form a dilute aqueous ethylene oxide and carbon dioxide solution and thereafter stripping that solution in an EO stripper to produce a gaseous ethylene oxide and carbon dioxide-containing overhead vapor which is then passed to a reabsorber wherein the ethylene oxide and part of the carbon dioxide vapors are absorbed to form an aqueous reabsorbate solution from which carbon dioxide is removed to produce an ethylene oxide-containing solution is improved by passing an impurities-containing liquid bleed stream obtained from the quench wash to a second, small quench bleed stripper where steam and carbon dioxide are added and gaseous overhead from that quench bleed stripper is passed to the reabsorber for recovery of the EO and removal of formaldehyde and other impurities.

10 Claims, 4 Drawing Sheets

METHOD FOR RECOVERY OF ETHYLENE OXIDE

This application is a national phase entry under 35 USC 371 of International Patent Application No.: PCT/US2019/032179 filed on 14 May 2019, which claims the benefit of U.S. Provisional Patent Application No. 62/680,210, filed on 4 Jun. 2018, the entire content of which is incorporated by reference.

The present application relates to an improved method for recovery of ethylene oxide as a high-purity absorbate stream and in particular to an improvement that will minimize the concentration of formaldehyde impurity in it.

FIELD OF THE INVENTION

This invention relates to a method of improving the purity of the ethylene oxide (EO) recovered from the gaseous effluent of an ethylene oxide reactor. Such effluent may be used for example as feed to EO Purification columns and/or to integrated glycol units for the production of polyester grade ethylene glycol (EG). More specifically, this invention relates to improved Quench absorption/stripping systems for recovery of ethylene oxide. Such systems are commonly used in the EO recovery step of integrated EO/EG plants that will produce a purer ethylene oxide-water feed for a high purity EO column or the glycol plant, together with substantial savings in both operating costs and simplifications in plant operation.

BACKGROUND OF THE INVENTION

When ethylene oxide is produced by silver-catalyzed, vapor-phase partial oxidation of ethylene by molecular oxygen, a hot gaseous reactor effluent is obtained. The ethylene oxide content is quite low, and recovery of the ethylene oxide from the effluent gas, as conventionally practiced, involves cooling of the reaction feed and product gases in a heat exchanger train and absorption in process water, producing a very dilute EO solution that also contains various absorbed impurities. Ethylene oxide is then stripped from this dilute solution in a stripping column that results in significant amounts of impurities such as formaldehyde mixed with the ethylene oxide which can be a problem for many applications, including preparation of ethylene glycol of a purity useful in the production of polyester fibers (fiber grade ethylene oxide). Ethylene oxide from the oxidation reactor is therefore frequently subjected to additional treatment either before or after the absorption/stripping treatment to improve its purity depending on its intended ultimate use.

In my U.S. Pat. No. 7,569,710, the EO reactor effluent is sent to an EO absorber. which contains a quench section in the lower part of the absorber column where it is scrubbed with a recirculated, cooled aqueous alkaline stream to absorb and neutralize acidic compounds such as acetic and formic acids and absorb almost all of the trace amount of by-product formaldehyde. Since the reaction gas contains $CO_2$, the alkaline aqueous quench stream consists of mainly sodium bicarbonate buffered with dissolved $CO_2$ (as carbonic acid) and has a pH in the range of 7.1-8.0. A quench bleed is then taken to remove the EO reaction by-product water, which is essentially totally condensed during the quenching. The treated vaporous reaction stream from the alkaline quench is passed through a demister and fed to a water wash section in which it is washed with fresh process water to remove any entrained quench liquid and absorb any remaining formaldehyde vapor, passed through liquid demister entrainment devices and fed to the bottom of the EO absorber where it is counter-currently washed with recirculated, EO-free process water to absorb the ethylene oxide and produce a high-purity EO-containing absorbate. The quench bleed, which contains typically 0.5-3.0 wt. % of EO and comparable concentrations of glycol and sodium salts as well as a low concentration of formaldehyde (as methylene glycol) is sent to a quench bleed stripper where EO is stripped out and recovered. The EO-free quench stripper bottoms can then be disposed of as a waste stream or processed separately for recovery of the small quantity of technical grade glycol that it contains.

The alkalinity of the recirculated, quench condensate stream is usually provided by sodium bicarbonate and carbonate, which are formed by the reaction of injected caustic solution with a small part of the $CO_2$ that is in the effluent gas from the EO reactor. Potassium hydroxide or carbonate can also be used instead of caustic but since they are more expensive than caustic, this would increase the chemical costs significantly. The design concentration range of the alkaline salts in the quench liquid for total neutralization of the organic acids in the reaction gas is typically in the range of 0.1-5.0 wt %. The low $CO_2$ concentrations that are currently required by modern, high performance EO reaction catalysts limit the $CO_2$ concentrations in the reaction cycle gas entering the Quench wash to 0.4-3.0% v which are equivalent to $CO_2$ partial pressures that are in the range of ca. 0.07-0.6 bar.

The published technical literature shows that even with 5.0 wt % of sodium bicarbonate plus carbonate in the recirculated quench solution and only 0.1 bar of $CO_2$ partial pressure, the equilibrium bicarbonate-to-carbonate molar ratio will be higher than 100:1. Since pure sodium bicarbonate in the quench solution would have a pH in the range 8.0-8.5 compared to pure sodium carbonate's pH range of 9.0-11.2, the initial pH of the pure bicarbonate-rich alkaline mixture in the quench solution would be in the range of ca. 8.2-9.0. However, since the quench solution will also contain absorbed $CO_2$ that forms carbonic acid, which acts as a buffer and lowers the pH by at least 1 unit, the resulting pH in the quench column will be in the range of 7.3-8.0, which is effective for the total neutralization of organic acids and the absorption of formaldehyde from the reaction gas (as confirmed by actual commercial operation).

As described in U.S. Pat. No. 7,569,710, the Quench bleed stripper is a small column which operates in parallel with the main EO stripper at near-atmospheric pressure and uses steam to strip out the absorbed EO. To avoid contaminating the main EO stripper product vapor with formaldehyde and entrained acid salts from the small purge stripper, the overhead EQ-rich vapor from the quench bleed stripper may need to be partially condensed and the contaminated condensate will be returned as reflux to the bleed stripper. The EO-free bottoms leaving the Quench bleed stripper should contain almost all the formaldehyde and heavy aldehydic impurities and all the (neutralized) acids produced in the EO reaction system and can be disposed of as a waste stream or processed separately for recovery of the contained small quantity of technical grade glycol.

In actual commercial operation, when the stripping vapor in the bottom of the quench bleed stripper is only steam that is directly injected or generated internally in a reboiler, the pH in the stripping section rises until it is in the range 9.0-10 due to the stripping of carbonic acid and the conversion of a significant portion of the sodium bicarbonate to sodium carbonate due to the absence of $CO_2$ in the stripping vapor. The literature surprisingly shows that at pH's above 8.0, the decomposition rate of methylene glycol will increase exponentially. As a result, most of the methylene glycol that is in the bleed stripper feed decomposes in the hot stripping section producing formaldehyde that is mainly stripped out so that the stripper bottoms purge contains only a small part of the aldehydes that are present in the feed to the stripper. The formaldehyde that is in the quench bleed stripper overhead vapor is then absorbed into the Reabsorber bottoms stream and significantly reduces the purity of the concentrated EO-water feed to EO Purification and/or the glycol plant.

The amount of formaldehyde that is purged in the quench bleed stripper bottoms can be increased and maximized by lowering the pH in the stripping section to less than 8.0, which radically reduces the methylene glycol decomposition rate in the stripping section. This can be done by injecting a dilute acid-water solution (such as acetic or sulfuric acid) to neutralize the excess sodium carbonate and bicarbonate in the quench bottoms bleed stream before it is fed to the quench bleed stripper. However, the necessary addition of acid storage, dilution, injection and pH control facilities will increase the investment and chemical costs and significantly complicate the operation of the Quench bleed stripper.

The present invention provides an equally effective, much less costly and much simpler design alternative to the injection of acid solutions to lower the pH in the Quench stripper to below 8.0, by injecting enough byproduct $CO_2$ vapor into the stripping steam to provide a minimum of 0.07 bar of $CO_2$ partial pressure.

SUMMARY OF THE INVENTION

Accordingly the present invention provides a method of purification of ethylene oxide which comprises quenching and washing the ethylene oxide reactor effluent by contact with a recirculated, cooled, aqueous alkaline stream, passing the gaseous ethylene oxide containing stream obtained from said quenching wash to an ethylene oxide absorber wherein the ethylene oxide is absorbed in once-through EO-free process water to form a dilute aqueous ethylene oxide- and carbon dioxide-containing absorbate solution and thereafter stripping said dilute absorbate solution in an EO stripper to produce a gaseous ethylene oxide and carbon dioxide-containing overhead vapor which is then passed to a reabsorber wherein the ethylene oxide and part of the carbon dioxide vapors are absorbed to form an aqueous reabsorbate solution, that is then passed to a carbon dioxide stripper to remove dissolved carbon dioxide with the lights-free, ethylene oxide-containing solution being recovered for use as high-purity feed to a EO Distillation system or a FG MEG reactor; and passing an impurities-containing liquid bleed stream obtained from said quench wash to a second, small quench bleed stripper, introducing steam and carbon dioxide into said second stripper, feeding the gaseous overhead from said quench bleed stripper to said reabsorber for recovery of the EO and removing the formaldehyde and impurity-containing bottoms from said quench bleed stripper.

In a preferred embodiment, the carbon dioxide fed to the quench bleed stripper is recycled carbon dioxide from other parts of the plant such as a rich carbonate flasher or carbon dioxide stripper in the $CO_2$ removal section.

In another preferred embodiment, from 10-90%, more preferably 20-80%, and most typically 25-30% of the dilute ethylene oxide solution obtained from the absorber is passed directly to the reabsorber, and never passes through the EO stripper, thus reducing the stripping steam consumed in the EO Stripper by 25-30%.

In a further preferred method, a separate quench column (or the bottom section of an EO absorber) is designed to thoroughly scrub the EO reactor effluent gas with recirculated, cooled, dilute alkaline solution, normally of 1 to 30%, preferably 1 to 15% solution of alkaline hydroxide, to neutralize the organic acids and absorb the maximum amount (ca. 90-98%) of the formaldehyde, and other soluble (in water) aldehydic impurities. Preferably the scrubbed gas from the alkaline quench-wash section will be passed through a high-efficiency, demister unit to remove entrained quench solution and will then be washed with a small amount of once-through (or recirculated) fresh water to remove any entrained quench liquid and absorb most of the remaining formaldehyde. The effluent wash water from the wash section then can drain into the lower quench section to reduce the concentration of formaldehyde and absorbed impurities and permit their more complete removal in the quench solution.

The washed cycle gas, which will be almost completely free of formaldehyde and heavy impurities and completely free of acids, will be typically be passed through a demister unit to remove entrained wash liquid and then thoroughly scrubbed in the EO absorber with once-through EO-free process water (recycled from the stripper and glycol unit) to completely absorb ethylene oxide and produce a dilute (1-5 wt. %) EO-water solution.

DETAILED DESCRIPTION OF THE INVENTION

Figure 1:
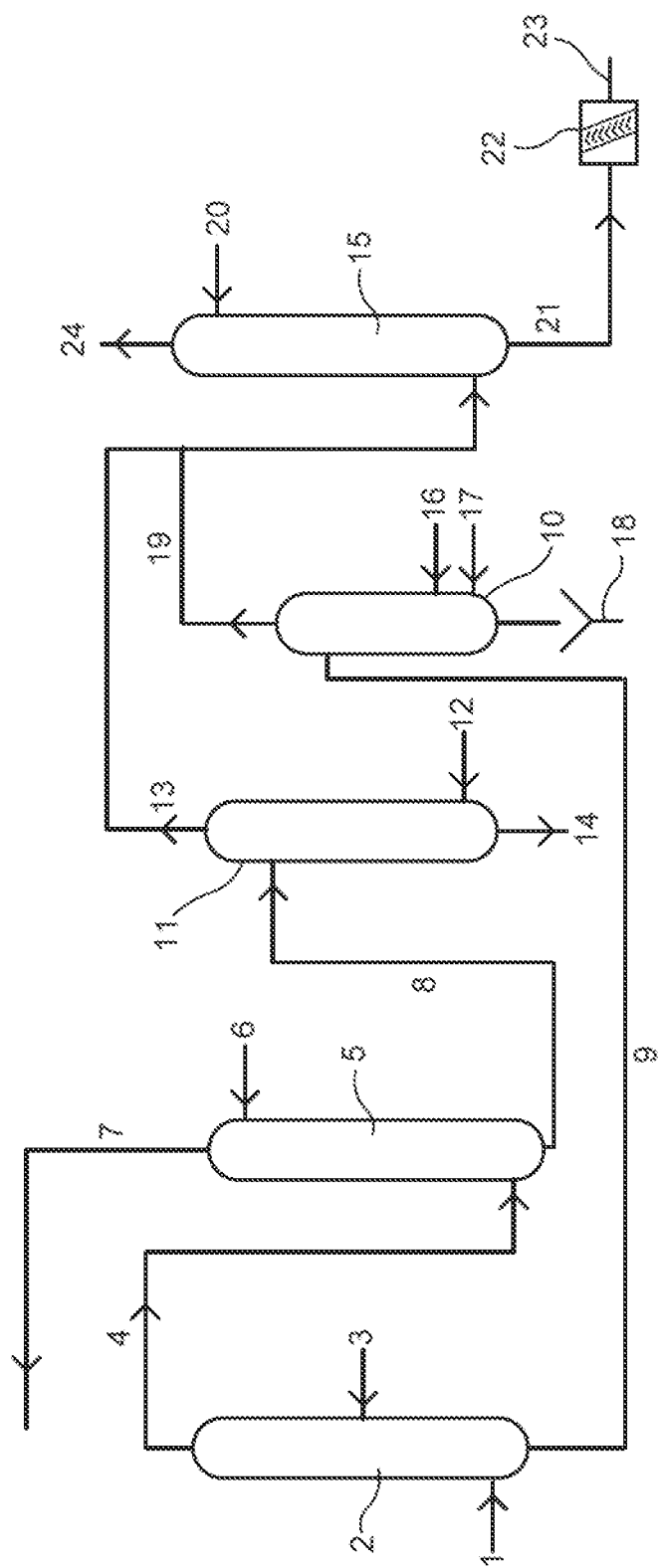
FIG. 1 is a schematic representation of a simple form of the present invention.

The simplest form of the invention is depicted in FIG. 1 wherein effluent from an ethylene oxide reactor is fed by line 1 into the lower part of quench column 2. Part of the quench bottoms is recirculated into the quench column after cooling, for example by passage through a heat exchanger.

Aqueous alkali, such as sodium hydroxide is fed into the quench column through inlet 3 located above inlet 1. The recycled portion of quench bottoms may conveniently be combined with the alkali and introduced through inlet 3, although this is not essential and a separate inlet for recycled bottoms may be provided. Commonly aqueous sodium hydroxide at a concentration of 10-20% by weight is used. Overhead from the quench column, including ethylene oxide is passed by line 4 to the bottom of the absorber 5. The net bottoms from the quench column are passed by line 9 to the upper part of purge stripper 10.

It is preferable to include demisters in the upper part of the quench column to minimize the amount of entrained liquid passed to the absorber. It is also possible to combine the quench column and the absorber in a single column wherein the absorber section is located above the quench section.

The upper part absorber 5 is fed with cold absorption water through inlet 6 and the reaction effluent gas is countercurrently contacted by the water to absorb almost all of the ethylene oxide entering via conduit 4. The non-condensable reaction gas leaving the top of absorber 5 is essentially free of ethylene oxide and is returned to the EO reaction system via conduit 7. The dilute EO-water solution that is formed in absorber 5 is withdrawn from the bottom of the absorption section via conduit 8 and passed to the top of the EO stripper 11. Steam is fed into the EO stripper through inlet 12. By countercurrent contact of the absorbate and steam within stripper 11, the absorbate is stripped of the ethylene oxide, which together with steam, carbon dioxide, light ends and trace impurities is withdrawn from the top of stripper 11 via conduit 13. The stripped (lean) absorbate, now essentially free of ethylene oxide, is withdrawn from the bottom of stripper 11 via conduit 14. If desired this lean absorbate may be cooled and recycled to absorber 5. The overhead from the stripper 11 contains ethylene oxide, together with steam, carbon dioxide, light ends, non-condensable gases and trace impurities. This overhead is passed via conduit 13 to the lower part of Reabsorber 15.

As noted above, the bottoms from quench column 2 are passed via conduit 9 to the upper part of purge stripper 10. As in conventional plants, steam is fed into the lower part of the purge stripper. According to the present invention, however, carbon dioxide is also introduced to the lower part of the purge stripper. The introduction of steam and carbon dioxide may be through separate inlets as shown in FIG. 1 as inlets 16 and 17 but preferentially the steam and carbon dioxide should be mixed and introduced together through a single inlet. The carbon dioxide is introduced in an amount to lower the pH in the purge stripper to below 8.0, by injecting enough byproduct $CO_2$ vapor into the stripping steam to provide a minimum of 0.07 bar of $CO_2$ partial pressure. More preferably, the pH is brought into the range 7.3 to 7.9 and the $CO_2$ partial pressure is in the range 0.1 to 0.3 bar. Conveniently, the carbon dioxide used may be recycled from other parts of the system. For example, the carbon dioxide may be obtained from the ethylene oxide production unit where it is removed from ethylene oxide in a $CO_2$ removal section. Such $CO_2$ removal sections can produce a vapor containing 95% or more carbon dioxide. Control of the pH in the purge stripper can be affected by monitoring the pH in the bottoms purge and adjusting the flow of $CO_2$ into the purge stripper. If the amount of $CO_2$ required to achieve the desired pH becomes too high, further adjustment of the pH may be effected by addition of an acid such as acetic or sulfuric.

Bottoms from the purge stripper 10 containing most of the formaldehyde, salts, and a small amount of ethylene glycol are sent via outlet 18 to waste treatment or technical grade glycol recovery. The overhead from purge stripper 10 containing ethylene oxide, steam and carbon dioxide is passed via conduit 19 to the reabsorber 15, optionally after having been combined with the overhead from stripper 11 in line 13. Cold water is introduced into the upper part of reabsorber 15 through inlet 20. Non-condensable gases are vented through vent 24. Bottoms from the reabsorber 15 are recovered through line 21 and after passing through carbon dioxide stripper 22, an ethylene oxide-containing stream is passed on to an ethylene glycol production reactor or further ethylene oxide distillation.

Most of the water formed in the EO reactor is condensed in the quench scrubber. To maintain the water balance in the quench water system, a net purge of the alkaline quench condensate plus wash water is required. Since the total quench bottoms purge will also contain a small concentration (1-4 wt. %) of EO, it will be shipped of its EO content in a small purge stripping column which will operate in parallel with the main stripper. To avoid contaminating the main stripper product EO vapor with formaldehyde and entrained acid salts from the small purge stripper, the overhead EO-rich vapor from the purge stripper will be partially condensed and the contaminated condensate will be returned as reflux to the purge stripper. The EO-free bottoms from the quench purge stripper will thus contain almost all of the formaldehyde and heavy aldehydic impurities and all the (neutralized) acids produced in the EO reaction system. Since the amount of glycol in this small purge (produced by hydration of EO in the quench scrubber and purge stripper) is extremely small, it usually does not justify the installation of dedicated purge glycol recovery facilities, and it can be sent directly to waste treatment in most plants. Alternately, the quench/wash purge could be processed for recovery of the glycol content as technical grade product.

The dilute EO-water bottoms stream from the absorber, which is free of organic acids, and essentially free of formaldehyde and heavy contaminants, will be completely stripped of EO and dissolved gases in the main EO stripper. The overhead EO and water-rich vapor is cooled and partially condensed in an overhead heat exchanger, which can be cooled using air or cooling water. Unlike the process described in U.S. Pat. No. 3,964,980, both the vapor and condensate effluent from the main stripper condenser is fed to the reabsorber, since the condensate which is rich in EO is also essentially free of impurities. This improves the efficiency of the EO stripping/reabsorption step compared to that of the prior art.

In this process, high-purity EO-water bottoms from the EO absorber would produce fibre-grade glycol if used as feed to an integrated glycol plant after removal of $CO_2$ and other absorbed non-condensable gases. Unfortunately, based on industry information, the concentration of ethylene oxide in the dilute EO absorbate is too low in commercial EO reaction systems to permit its economical use as direct feed to a glycol reactor and evaporation system.

The water balance in the absorber-stripper system may be maintained by injecting low pressure process steam extracted from the glycol plant directly into the EO stripper to provide up to 100% of the stripping vapor required (which is an additional benefit of this invention) or by recycling water from the glycol plant evaporation section for use as absorption water.

Figure 2:
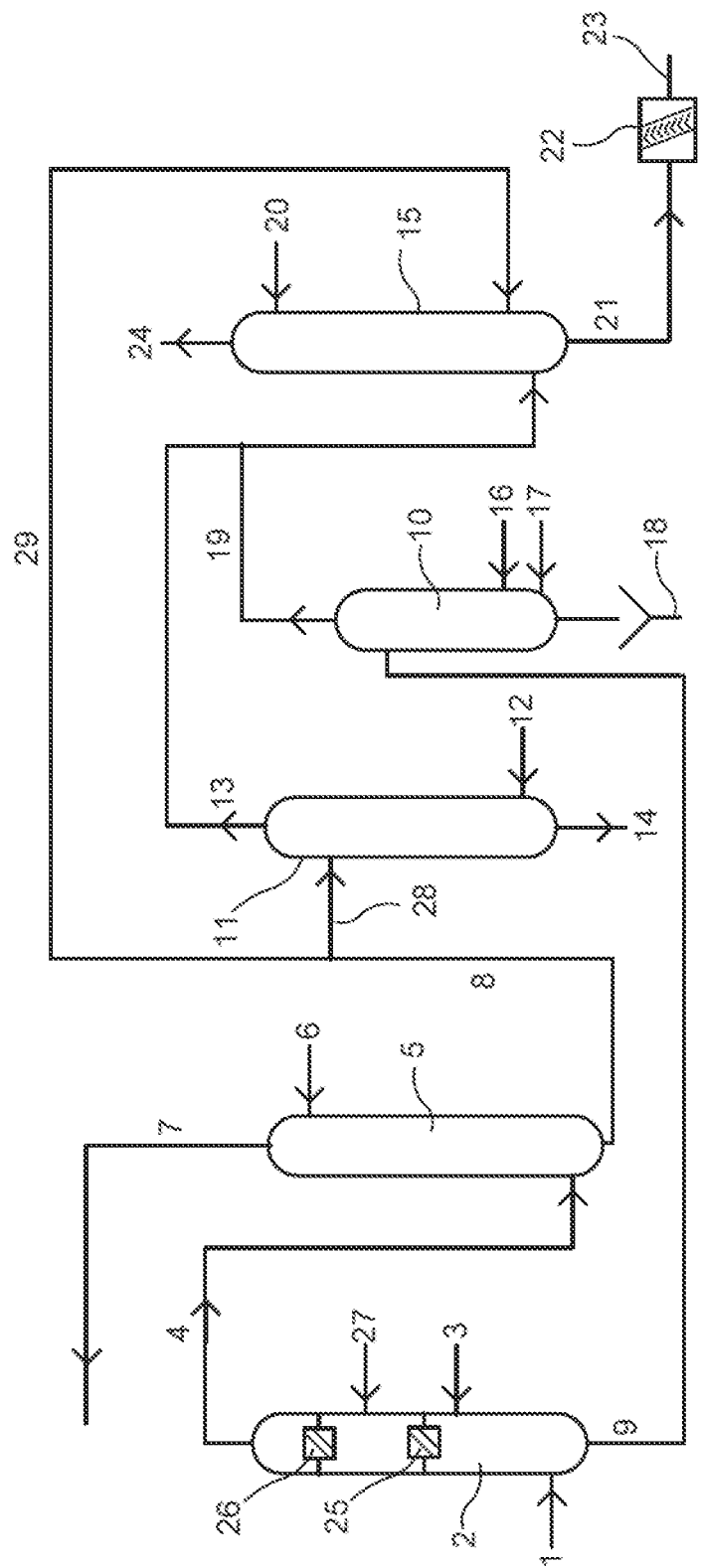
FIG. 2 is a schematic representation incorporating all of the preferred features noted above, although it should be recognized that each of these preferred features may be employed independently of each other.

In a preferred method of the present invention as shown in FIG. 2, a substantial portion of the EO absorbate does not need to be stripped of its EO in the main EO stripper and can be sent directly to the EO reabsorption system to absorb more ethylene oxide so that it can then be used as direct feed to the glycol reactor or an HPEO column. This reduces the operating and capital cost of the EO absorption system and also makes the use of water/EO molar ratios that are higher than 25:1 more economical.

The flow scheme depicted in FIG. 2 includes all of the preferred features noted above, although as pointed out previously each of the preferred features may be used independently of the other. Parts common to FIGS. 1 and 2 have the same reference numerals in both figures.

The flow scheme in FIG. 2 differs from that in FIG. 1 in the following ways:

1) The quench column 2 is provided with demisters to remove entrained liquids from the gaseous stream being passed to absorber 5. Commonly two demisters are used, although the actual number may vary depending on the conditions being used. When two demisters are employed, they will be located in the quench tower one above the other with a fresh water feed located between them. Thus, in the quench column 2 of FIG. 2 material rising from the quench section below the alkali feed inlet is first passed through demister unit 25, washed with fresh water fed through inlet 27 and then passed through an upper demister unit 26 before leaving the quench column through overhead conduit 4. Water added in this way is included in the quench column bottoms that is fed to the purge stripper 10. Normally the major portion of the quench bottoms removed by line 9 will be cooled and recycled to the quench column below the lower demister mesh 25.

2) As described in U.S. Pat. No. 7,569,710, a large part of the energy costs in ethylene oxide recovery units lies in the conventional stripping of all of the material passing from the absorber if ethylene oxide of a purity sufficient for production of fiber grade ethylene glycol or some other uses is desired. The invention described in U.S. Pat. No. 7,569,710 is based on the insight that ethylene oxide of the desired purity can be obtained even if only a portion of the absorbate from the absorber is passed through the stripper. This insight is equally applicable to the present invention. In the flow scheme of FIG. 2, absorbate from absorber 5 passing through line 8 is split between two conduits. Some passes through conduit 28 into the stripper and the remainder passes through conduit 29 to the reabsorber 15. Typically. of the dilute ethylene oxide solution obtained from the absorber 5 is passed direct to the reabsorber 15 and. Accordingly, in a commercially significant feature of one aspect of this invention, from 10-90%, preferably 20-80%, and most commonly 25-30% of the impurity-free. EO absorber bottoms can be fed directly into the reabsorption system, bypassing the EO stripper and then passed on to the removal of dissolved carbon dioxide without ever passing through the EO stripper. The maximum potential stripper bypass rates (and the related stripper savings) increase as the concentration of EO in the absorbate increases, and as the water to-EO ratio in the glycol reactor feed is raised to reduce the production of heavier glycols. The flowrate of reabsorption feed water, which may be recycled water from the glycol plant evaporation (and EO purification section), is reduced proportionately to produce the desired concentration of EO (typically 6-12 wt. %) in the reabsorber (or light ends column) bottoms.

3) Carbon dioxide introduced to the purge stripper 10 is recycled from the carbon dioxide removal section via line 17 and mixed with steam from line 16 before being injected into the stripping section.

As noted above, it may be useful to recycle the bottoms from stripper 11 after cooling to the top of the absorber 5. If this is done, it may be useful to pass the hot bottoms from the stripper passing through outlet 14 through a heat exchanger in which it heats the material being fed into the top of the stripper 11.

The method of the present invention is applicable to both SD and Shell type ethylene oxide recovery systems as described above to adjust the pH level in what is referred to typically as a purge stripper on the SD method or a quench bleed stripper in the Shell method.

In embodiments wherein substantial amounts of absorbate bypass the stripper and pass direct to the reabsorber, a further major saving for improved SD-type EO flow schemes results from elimination of the costly stripper bottoms (cycle water) bleed treating systems such as described in U.S. Pat. No. 3,904,656 or separate byproduct glycol concentration and recovery facilities described in U.S. Pat. No. 6,417,411.

The improved stripper bypass flow scheme permits very high "bleed" rates of EO cycle water to the glycol plant without costly pretreatment. As a result, the equilibrium glycol concentration in the EO absorber-stripper cycle water can be reduced to very low concentrations (<1 wt. %) compared to the much higher concentrations (3-6 wt. %) that are typical for standard stripper systems. The lower MEG concentration reduces the foaming tendency of the water absorbent in both the EO absorber and the EO stripper and thus increases the capacity and efficiency of the trays or packing in those columns. Thus the application of this invention to EO absorber-stripper systems in new plants will save both initial investment capital and continuous energy usage.

The stripper bypass concept can also have great benefits for existing EO plants that wish to expand the capacity of their existing EO reaction and recovery sections. The application of this invention will debottleneck the EO absorber-stripper system very simply, at minimum capital cost, and also provide significant reduction in energy consumption (and $CO_2$ production), which has now become a major environmental as well as economic consideration.

The removal of essentially all the formaldehyde produced in the EO Reactor from the feed steams to the glycol unit will result in the production of fewer UV-absorbing impurities in the glycol reactor and improve the fiber-grade glycol quality. Accordingly, another major potential benefit of the application of this invention to SD-type EO reaction/recovery systems similar to that described in U.S. Pat. No. 3,964,980, is that it would permit the use of ultra-high selectivity EO catalysts, which (as is known in the industry) may generate high amounts of formaldehyde that would normally adversely affect the UV quality of glycol produced in standard SD-type integrated glycol units that produce only fiber grade MEG.

The Shell type EO process, as described in U.S. Pat. No. 4,822,926, includes a quench scrubber and quench stripper, which are essential steps of the improved EO recovery process. However, these two process steps, as described in the patent, cannot produce EO absorber bottoms that are completely contaminant-free and suitable as direct feed to a fiber grade glycol reactor, and in the patent flow scheme, 100% of the EO absorbate is ultimately fed to the EO stripper. By incorporating this invention and increasing the impurity absorption efficiency of the quench section by adding a water wash and reducing inter-stage and inter-section entrainment in the quench-wash column, the rich EO absorbate will be pure enough for use as direct feed to the glycol plant. As a result, a significant portion (15-75%) of the EO absorbate can then be injected directly into the stripper overhead EO recovery section to absorb more EO and then fed directly to the EO Purification column, thus completely bypassing the EO stripper.

In addition, to avoid any contamination from the quench bleed solution in the present improved flow scheme, the EO-rich overhead vapor from the quench stripper (e.g., in the Shell process) will be partially condensed and the condensate, contaminated with entrained salts and condensed formaldehyde, will be returned as reflux to the quench stripper. The net ethylene oxide vapor and uncondensed steam will flow directly to the residual EO absorber for recovery of the EO vapor as glycol reactor feed. The EO-free bottoms from the improved quench bleed stripper will then contain essentially all of the formaldehyde and heavy aldehydic impurities and all the (neutralized) acids produced in the EO reaction system. Since the amount of glycol in this small purge (produced by hydration of EO in the quench scrubber and stripper) is extremely small, it can be sent directly to waste treatment with minimum economic loss if existing purge glycol recovery facilities are not available.

The current UV transmittance sales specifications, which are as follows:

|  | UV Transmittance % |
| --- | --- |
| At 220 nm | 80 min |
| At 275 nm | 95 min |
| At 350 nm | 99 min |

The major contributor to the production of impurities in the glycol hydration reactor, which adversely affect the UV transmittance of the fiber grade ethylene glycol product is the formaldehyde that is introduced via the treated cycle water bleed and that builds up in the glycol reaction recirculated water.

Figure 3:
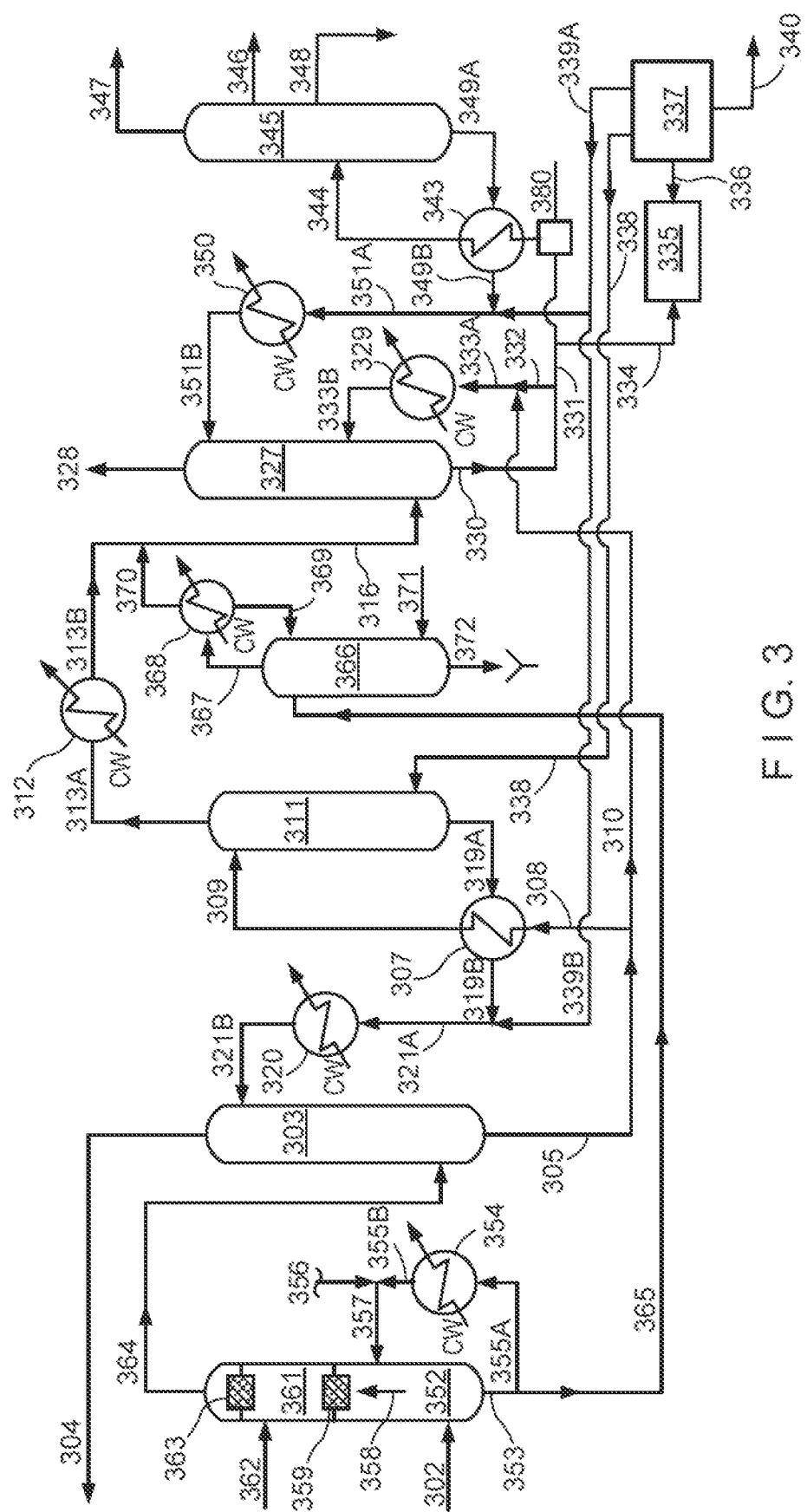
FIG. 3 is a schematic representation of the incorporation of the improved process into the flow scheme of a prior art recovery system such as that described in U.S. Pat. No. 3,964,980, which consists of the new wash/quench column and the quench purge stripper, and the addition of a rich EO absorbate stream that bypasses the EO Stripper and flows directly to the EO reabsorber and, after $CO_2$ and lights removal, on to the HPEO column and/or the MEG reactor.

The embodiment of this invention as applied to plants described in U.S. Pat. No. 3,964,980, is shown in FIG. 3. Referring to FIG. 3, effluent gas from the EO Reaction system containing ethylene oxide is introduced directly into the bottom section of quench column 352 via conduit 302. Quench bottoms solution is recirculated via conduits 353 and 355A, cooler 354, and conduits 355B and 357 to the top of the quench scrubbing section. Concentrated sodium hydroxide (10-20 wt. % aqueous solution) is injected into the recirculated quench solution via conduit 356 to be converted into sodium carbonate and bicarbonate and neutralize organic acids. The cooled, scrubbed vapor from the top of the quench section 352, which is free of organic acid vapor but contains some formaldehyde and entrained quench liquid is passed through a demister unit 359 to remove the entrained liquid and enters the upper wash section 361.

The filtered quench gas leaving the quench demister 359 is then washed with fresh process water, introduced via conduit 362 to completely remove any remaining entrained quench liquid and absorb most of the remaining formaldehyde and heavy impurities. A countercurrent water wash will preferably be used, which can be preceded by a recirculated water wash section for maximum vapor-liquid contact. The net wash water from the bottom of the water wash section(s) may drain into the top of the lower quench section 352, diluting the concentration of formaldehyde and other undesirable impurities in the quench liquid and reducing the equilibrium concentration of these impurities in the scrubbed gas feed to the EO absorber. The net quench bottoms solution bleed, containing condensed water, wash water, absorbed impurities and some ethylene oxide, flows via conduits 353 and 365 to quench bleed stripper 366.

The washed vapor from the top of the water wash section, is passed through demister unit 363 to remove any entrained wash water and enters the bottom of the EO absorber 303 via conduit 364. Cold absorption water is introduced into the upper section of absorber column 303 via conduit 321 B and the reaction effluent gas is counter currently contacted by the water to absorb almost all of the ethylene oxide entering via conduit 364. The non-condensable reaction gas leaving the top of absorber 303 is essentially free of ethylene oxide and is returned to the EO reaction system via conduit 304. The dilute EO-water solution that is formed in absorber 303 is withdrawn from the bottom of the absorption section via conduit 305.

In FIG. 3 the quench/wash column is shown as a separate vessel for clarity of depiction. However in actual plants, the EO absorber, water wash, and alkaline quench sections can be combined into one shell to minimize pressure drop and capital cost.

In this flow scheme part of the EO absorbate in conduit 305 bypasses EO stripper 311 and flows directly to the EO reabsorber bottoms recycle cooler 329 via conduits 310 and 333A. The amount bypassed will vary between 15-75% depending on the EO concentration in the absorbate and the desired EO concentration in the reabsorber bottoms (and glycol reactor feed), and can be determined using tables, equations, or graphs.

The balance of the absorbate is introduced into the stripper preheater exchanger 307 via conduit 308, and the hot rich absorbate from preheater 307 is fed to an upper portion of EO stripper 311, via conduit 309. Stripping steam extracted from the glycol plant is introduced to a lower portion of stripper 311 via conduit 338 or generated internally by a reboiler (not shown). By countercurrent contact of the absorbate and steam within stripper 311, the absorbate is stripped of the ethylene oxide, which together with steam, carbon dioxide, light ends and trace impurities is withdrawn from the top of stripper 311 via conduit 313A. The stripped (lean) absorbate, now essentially free of ethylene oxide, is withdrawn from the bottom of stripper 311 via conduit 319A and cooled in heat exchanger 307, giving up heat to the rich absorbate feed. The cooled lean absorbate from cooler 307 is passed via conduit 319B, combined with recycled water from the glycol plant in conduit 321A to heat exchanger 320, where it is further cooled and the total lean absorbate stream is recycled back to absorber 303 via conduit 321 B.

The rich absorbate feed to stripper 311 may contain from about 1 to about 5 wt. % of ethylene oxide and the stripper is operated to recover more than 95% and usually more than 99% of the ethylene oxide contained in the stripper feed. Though the stripper normally operates at close to atmospheric pressure, the temperatures in the column are high enough to thermally hydrate in the range of 0.5-3.0% of the EO feed to ethylene glycol. The glycol produced in the EO stripper will build up to a low, equilibrium concentration that is controlled by the absorbate bypass (via stream 310), which acts as a very large cycle water glycol bleed.

The stripper overhead vapor withdrawn via conduit 313A usually contains about 20 to 30 mole % of ethylene oxide. The primary diluent in this vapor stream is water, although about 7-10% can be generally referred to as non-condensable gases, predominantly $CO_2$, but also including nitrogen, argon, oxygen, methane, ethylene and ethane. The stripper overhead vapors are cooled in heat exchanger 312 and the total effluent mixture of uncondensed vapor and condensate flows via conduits 313B and 316 to the reabsorber 327.

The net bleed bottoms stream from quench column 352 consists mainly of the EO reaction byproduct water that is partially condensed in the quench scrubber plus makeup wash water, and contains some alkaline salt and absorbed ethylene oxide. This stream is sent, via conduit 365, to a small purge stripper 366 where the contained ethylene oxide is stripped out, using stripping steam injected via conduit 371, or generated in a reboiler (not shown). A purge stripper feed/bottoms heat exchanger may be also used to reduce the reboiler heat duty and/or the amount of stripping steam. The purge stripper overhead vapors are cooled in heat exchanger 368 to a temperature such that a substantial part, preferably at least 60%, of the contained water is condensed. The contaminated condensate phase from condenser 368 is drained or pumped back into the upper portion of the purge stripper 366 via conduit 369. The uncondensed purge stripper overhead vapor is withdrawn from condenser 368 via conduit 370, combined with the EO and condensate mixture from main stripper condenser 312 in conduit 316 and introduced into a lower portion of the reabsorber 327. The EO-free aqueous bottoms from purge stripper 366, containing most of the formaldehyde, salts, and a small amount of ethylene glycol are sent to waste treatment or technical grade glycol recovery via conduit 372.

Some recycle cold water is introduced to an upper portion of reabsorber 327 via conduit 351 B. Within the upper portion of the reabsorber, the light gases in the stripper overhead vapor and the water are counter-currently contacted to absorb the maximum amount possible of the ethylene oxide contained in the vapor. The non-condensed gases from the top of reabsorber 327, normally containing only trace amounts of ethylene oxide are vented via conduit 328. Since this vent stream contains a significant amount of hydrocarbons, consisting mainly of ethylene and methane, it is preferably compressed and recycled back to the ethylene reactor gas system for (partial) recovery of the contained ethylene. In some plants, particularly those of small production capacity, the reabsorber vent gas is vented to atmosphere, or preferably incinerated to avoid atmospheric pollution.

The EO-ich reabsorbate is withdrawn from the bottom of reabsorber 327 via conduit 330. The reabsorbate is pressurized using a pump (not depicted) and divided into two portions. The portion which is the net bottoms product flows through conduits 331 and 334 to the glycol reaction system 335 and/or may flow via conduit 344 to EO purification unit 345. The aqueous reabsorbate bottoms contain not only the reabsorbed ethylene oxide vapor but also contain acetaldehyde and dissolved carbon dioxide and non-condensable gases. The water balance in the absorber-stripper system may be maintained by injecting low pressure process steam extracted from the glycol plant directly into the EO stripper to provide up to 100% of the stripping vapor required (which is an additional benefit of this invention) or by recycling water from the glycol plant evaporation section for use as absorption water and other organic and inorganic gases.

As described in U.S. Pat. No. 4,134,797, the EO-rich reabsorbate withdrawn via conduits 330 and 331 will first pass into a carbon dioxide stripping column 380, wherein the liquid is stripped of $CO_2$. The gas-free bottoms from the carbon dioxide stripping column are then pumped to the glycol reaction and EO purification units, as described in U.S. Pat. No. 3,964,980.

The recycled reabsorbate flowing through conduit 332 is combined with bypassed rich absorbate in conduit 333A, cooled in heat exchanger 329 and introduced as cold liquid to a middle portion of reabsorber 327 via conduit 333B. Heat exchanger 329 maintains the reabsorber in heat balance to achieve the pre-determined bottom reabsorbate temperature and concentration of ethylene oxide. Depending on the operating pressure of the reabsorber and the amount of bypassed dilute absorbate, the ratio of reabsorbate recycled via conduit 332 to the net reabsorbate withdrawn via conduit 331 will range from 0-3:1. The maximum bypass of rich absorbate (not shown) may be achieved when the bypassed absorbate in stream 310 is separately cooled and introduced into reabsorber 327 at a point above the recycled bottom reabsorbate.

The reabsorbate flowing to EO purification is preheated in heat exchanger 343 and fed to the lower part of a single EO purification column 345 where it is separated into a purified EO product (stream 346), and two formaldehyde and acetaldehyde-rich crude EO purge streams (streams 347 and 348, respectively) which are fed to the glycol reactor 335. The EO-free bottom water stream containing most of the trace amount of formaldehyde in the purification feed, is withdrawn via conduit 349A, cooled in heat exchanger 343 and recycled to the reabsorber 327 via conduit 349B.

In the glycol reactor 335, the ethylene oxide in the degasified reabsorber bottoms is almost completely reacted with water to form ethylene glycols. The effluent from the glycol reactor 335, is fed to a multiple-effect evaporation train 337 in which the water is separated from the crude glycol that is then fed to glycol purification (not shown) via conduit 340. Part of the water separated in evaporation train 337 is recycled back to the EO plant as steam via conduit 338 and injected directly into EO stripper 311 to provide up to 100% of the required stripping steam. The balance of the recovered water is condensate that is recycled back to the EO plant via conduits 339A and 342, combined with EO refiner 345 bottoms in conduit 351A, cooled in cooling unit 350 and fed to the top of reabsorber 327 as the reabsorbate via conduit 351 B. To maintain the water balance in the EO stripper 303, makeup glycol recycle water can be added via conduits 339B, 321A and 321 B.

The improved flow scheme depicted in FIG. 3 and described herein will produce fiber grade MEG that will significantly exceed the current UV transmittance sales specifications, which were shown previously.

Figure 4:
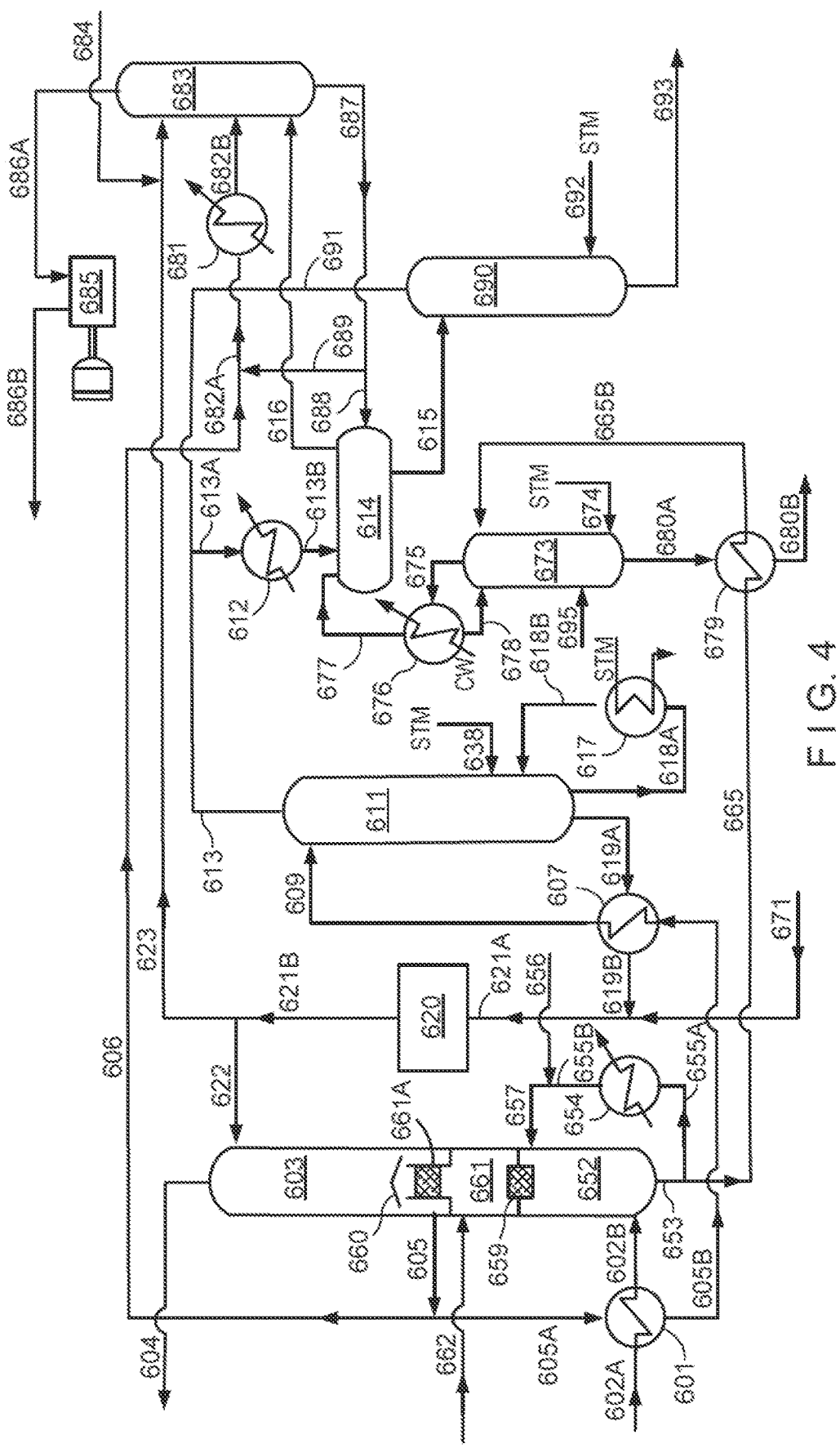
FIG. 4 is a schematic representation of the incorporation of the improved process into the flow scheme of a prior art recovery system such as that described in U.S. Pat. No. 4,822,926, which consists of the improved wash/quench column and modified EO stripping system, with the injection of the rich EO absorbate stripper by-pass stream into the residual absorber to absorb more EO before being fed directly to the HPEO column.

The embodiment of this invention as applied to integrated EO/EG plants with an EO recovery flow scheme comparable to that U.S. Pat. No. 4,822,926, is shown in FIG. 4. Referring to FIG. 4, effluent gas from the EO Reaction system containing ethylene oxide is passed via conduit 602A, gas cooler 601, and conduit 602B into EO quench section 652 of the EO absorption column, as before. Quench bottoms solution is recirculated via conduits 653 and 655A, cooler 654, and conduits 655B and 657 to the top of the quench scrubbing section 652. Sodium hydroxide is injected via conduit 656 into the recirculated quench solution to be converted into sodium carbonate and bicarbonate and neutralize organic acids. In a new plant, the gas cooler 601 can be omitted by increasing the quench recirculation rate and the heat duty of the quench cooler, and by the addition of 1-4 more quench trays.

The cooled, scrubbed vapor from the top of quench section 652, which is free of organic acid vapor but contains some formaldehyde and entrained quench liquid is passed through a demister unit 659 to remove the entrained liquid and enters the upper wash section 661 via an internal vapor conduit (not shown). The filtered quench gas leaving quench demister 659 is then washed with fresh process water (stream 662) to completely remove any remaining entrained quench liquid and absorb most of the remaining formaldehyde and heavy impurities. A countercurrent water wash will preferably be used, which can be preceded by a recirculated water wash section for maximum vapor-liquid contact. The net wash water from the bottom of the water wash section(s) 661 can drain into the top of the lower quench section 652, diluting the concentration of formaldehyde and other undesirable impurities in the quench liquid and reducing the equilibrium concentration of these impurities in the scrubbed gas feed to the wash section. The net quench bottoms solution bleed, containing condensed water, wash water, alkaline salts, absorbed impurities and some ethylene oxide, flows via conduits 653 and 665 to quench bleed stripper 673. Concentrated $CO_2$ that is injected into the quench bleed stripper via line 695 to lower the pH is preferably mixed with steam from line 674. The $CO_2$ is available from the $CO_2$ Removal Section of the ethylene oxide production unit. The pH is controlled in the range 7.3-7.9 by monitoring the pH and adjusting the flow of $CO_2$ into the purge stripper. If the amount of $CO_2$ required to achieve the desired pH becomes too high, further adjustment of the pH may be affected by addition of an acid such as acetic or sulfuric.

The washed vapor from the top of the water wash section, is passed through demister 661 A to remove any entrained wash water and enters the bottom of EO absorber 603 via internal conduit 660. In EO absorber 603, the EO contained in the quenched reaction gas is absorbed by countercurrent contact with cold, recycled absorption water introduced via conduit 622. The non-condensable reaction gas leaving the top of absorber 603 is essentially free of ethylene oxide and is returned to the EO reaction system via conduit 604. The EO-rich absorption bottoms exit via conduit 605, and a portion (15-75%) bypasses the EO stripper and is sent directly, via conduits 606, 682A and 682B and new reabsorption cooler 681, to the middle section of the residual absorber 683 where it absorbs more ethylene oxide.

The balance of the rich absorbate flows via existing conduit 605A to gas cooler 601 and enters stripper preheater exchanger 607 via conduit 605B. The hot rich absorbate from preheater 607 is introduced into the upper part of EO stripper 611, via conduit 609. In EO stripper 611, the dissolved ethylene oxide and other light components are stripped out using stripping steam generated in reboiler 617 and/or injected directly as live steam (stream 638). The stripped (lean) absorbate, now essentially free of ethylene oxide, is withdrawn from the bottom of stripper 611 via conduit 619A and cooled in heat exchanger 607, giving up heat to the rich absorbate feed. The cooled lean absorbate from cooler 607 is passed via conduit 619B, combined with recycled water from glycol evaporation and EO purification (stream 671) in conduit 621A to cooling unit 620, where it is further cooled and recycled back to absorber 603 via conduits 621B and 622. A portion of the cold lean absorbate from cooler 620 can be sent via conduit 623 to the top of residual absorber 683 to absorb ethylene oxide from the light gas vent. Alternatively, cold recycled water from the glycol and EO purification units (stream 684) could be injected directly into reabsorber to replace all or part of stream 623.

The stripper overhead vapor withdrawn via conduit 613 can be expected to contain about 20 to 30 mole % of ethylene oxide. The primary diluent in this vapor stream is usually water, although about 7-15% are non-condensable gases, predominantly $CO_2$, but also includes nitrogen, argon, oxygen, methane, ethylene and ethane. The stripper overhead vapors are combined with the overhead vapor from the light ends column 690 in conduit 613A and are cooled and partially condensed in heat exchanger 612. The total effluent mixture of uncondensed vapor and condensate from condenser 612 flows via conduit 613B into separator 614 where the vapor and liquid are separated.

The EO-rich vapor flows from separator 614 via conduit 616 to the bottom portion of residual absorber 683. Within the top portion of residual reabsorber 683, the light gases in the stripper overhead vapor are counter-currently contacted by cold recycle water to absorb the maximum amount possible of the ethylene oxide contained in the vapor. The non-condensed gases from the top of reabsorber 683, normally containing only trace amounts of ethylene oxide are vented via conduit 686A. Since this vent stream contains a significant amount of hydrocarbons, consisting mainly of ethylene and methane, it is preferably compressed in compressor 685 and recycled back to the ethylene reactor gas system for recovery of the contained ethylene. In some plants of small production capacity, the residual absorber vent gas may be vented to atmosphere or, preferably, incinerated to avoid atmospheric pollution.

The EO-rich reabsorbate is withdrawn from the bottom of residual absorber 683 via conduit 687. The reabsorbate is pressurized using a pump (not depicted) and divided into two portions. The portion which is recycled flows through conduit 689 and after combining with the bypassed rich absorbate in conduit 682A, is cooled in heat exchanger 681 and enters the mid-section of residual reabsorber 683. The net reabsorbate product flows via conduit 688 to separator 614 where it is combined with the condensate from condenser 612 and enters the upper part of the light ends column 690 via conduit 615. In light ends column 690 the reabsorbate solution is stripped of $CO_2$ and other dissolved gases which are recycled back via conduit 691 and 613A to condenser 612.

All the lights-free bottoms from light ends tower 690 are then pumped directly to the glycol reaction and EO purification units (not shown) via conduit 693.

The improved EO quench/wash system of the present invention reduces formaldehyde and other contaminants in EO absorbate making it suitable as direct feed to glycol reaction, and improving MEG quality. Also, the improved EO quench cooling system design afforded by the improved quench/wash system permits the omission of reaction gas cooler and reduces cycle gas pressure drop, saving power. The improved quench purge column design reduces contamination of EO reabsorbate feed to glycol reaction and improves MEG quality. Other glycol reaction improvements resulting from the present invention include: raising the economically optimum range of water/EO ratios in the glycol reactor feed (EO reabsorbate) by increasing the effective EO stripper bypass, making the use of very high water ratios (up to 40:1) justifiable, resulting in reduced DEG/TEG production with higher yields of MEG; injecting extracted low pressure process steam from the glycol plant directly into the bottom of the EO stripper provides up to 100% of the required stripping steam; Sending the aqueous bleed stream from the quench/wash section to a separate purge stripper, designed for low liquid holdup time to minimize EO hydration to MEG, in which absorbed EO is completely stripped out for recovery as feed to the fiber-grade MEG reactor; Cooling the purge stripper overhead vapors to condense a substantial part (preferably at least 60%) of the water vapor and returning the condensate, contaminated with entrained salts and condensed formaldehyde, back to the top of the purge stripper. The uncondensed EO-rich vapor from the partial condenser is then pure enough to be combined with the main EO stripper overhead vapor for recovery of its EO content in the reabsorber or residual absorber.

Elimination of need for prior glycol treatment systems saves capital and operating cost. The present incorporation of quench/wash and quench purge stripper system purges most of formaldehyde made in EO reaction to waste and radically reduces a formaldehyde buildup in glycol reaction system which permits use of ultra-high selectivity EO catalysts. As the water/EO ratio in glycol reactor feed (EO reabsorbate) is increased, the stripper bypass can be increased, making the use of very high water ratios (up to 35:1) economically justifiable and resulting in higher yields of MEG.

A high "purge" rate of stripper cycle water to glycol plant results in very low equilibrium glycol concentration in cycle water with reduced foaming and improved column efficiency and capacity and permits direct injection of very low pressure process steam extracted from glycol plant into EO stripper to provide up to 100% of the required stripping steam.

The invention claimed is:

1. A method of purification of ethylene oxide which comprises:
   quenching and washing ethylene oxide reactor effluent by contact with aqueous alkali, passing a gaseous ethylene oxide containing stream obtained from said quench/wash to an ethylene oxide absorber wherein the ethylene oxide is absorbed in water to form a dilute aqueous ethylene oxide and carbon dioxide-containing solution and thereafter stripping said dilute solution in a EO stripper to produce a gaseous ethylene oxide and carbon dioxide-containing overhead vapor which is then passed to a reabsorber wherein ethylene oxide and carbon dioxide are absorbed to form a concentrated aqueous solution, the reabsorbate then being passed to a carbon dioxide and lights stripper to release gaseous carbon dioxide and the ethylene oxide-containing solution being recovered for use or further treatment; and passing an purities-containing liquid stream obtained from said quench/wash to a second stripper such as a purge stripper or quench bleed stripper, introducing steam and carbon dioxide into said second stripper, feeding the gaseous overhead from said quench bleed stripper to said reabsorber and removing the impurity-containing bottoms from said quench bleed stripper, wherein the $CO_2$ vapor is fed into the stripping steam to provide a minimum of 0.07 bar of $CO_2$ partial pressure and/or the pH in the second stripper after feeding carbon dioxide to it is below 8.0.

2. The method as claimed in claim 1, wherein the carbon dioxide fed to the second stripper is recycled carbon dioxide obtained from a point downstream of the residual absorber.

3. The method as claimed in claim 1, wherein from 10-90%, of the dilute ethylene oxide solution obtained from the absorber is passed directly to the reabsorber without ever passing through the stripper.

4. The method as claimed in claim 1, wherein a separate quench column (or the bottom section of an absorber) is provided to thoroughly scrub the EO reactor effluent gas with recirculated, cooled, dilute alkaline solution, of 1 to 30%, solution of alkaline hydroxide, to neutralize the organic acids and absorb the maximum amount (ca. 90-98%) of the formaldehyde, and other heavy (in water) aldehydic impurities.

5. The method as claimed in claim 4, wherein the scrubbed gas from the quench section is passed through a high-efficiency, demister unit to remove entrained quench solution and will then be washed with a small amount of once-through (and/or recirculated) fresh water to remove any entrained quench liquid and absorb more formaldehyde.

6. The method as claimed in claim 1, for recovering ethylene oxide from a vaporous reaction stream containing ethylene oxide, CO2, formaldehyde, acetaldehyde, and organic acidic compounds comprising: absorption of ethylene oxide and a portion of said CO2, formaldehyde, acetaldehyde, and organic acidic compounds in water to form an absorption stream; contacting said absorption stream with steam to strip ethylene oxide, CO2, formaldehyde, acetaldehyde, and organic acidic compounds from said absorption stream to form a stripper overhead vapor stream; condensing water, formaldehyde, a portion of the ethylene oxide, acetaldehyde and organic acidic compounds; and recovering a vaporous ethylene oxide product stream; and contacting the vaporous ethylene oxide product stream in an EO absorber where it is counter currently washed with recirculated EO-free process water to absorb the ethylene oxide to produce EO containing absorbate: wherein the improvement comprises sending a portion comprising 10-90% of the dilute EO containing absorbate from the EO absorber directly to a EO reabsorber/residual absorber where said dilute EO containing absorbate absorbs additional EO from an EO stripper overhead vapor to produce an EO/water solution of the desired high EO concentration suitable for use as feed to an EO Purification column or a glycol production reaction system, reducing the quantity of stripping steam required in the EO stripper in direct proportion to the amount of EO absorbate that bypasses the EO Stripper.

7. The method as claimed in claim 1, wherein vaporous reaction stream from an alkaline Quench wash section is fed to a water wash section in which it is washed with fresh process water and demisted before being fed to the bottom of the EO absorber where it produces a high purity EO-containing absorbate of which 10-90% can be sent directly to an EO Reabsorber to absorb more EO and produce a more concentrated high purity EO-water solution that can then be fed to the glycol reaction section for the production of fiber-grade MEG, or to an HP EO Column for the production of high-purity EO.

8. The method as claimed in claim 3, wherein from 20-80% of the dilute ethylene oxide solution obtained from the absorber is passed directly to the reabsorber without ever passing through the stripper.

9. The method as claimed in claim 8, wherein from 25-30% of the dilute ethylene oxide solution obtained from the absorber is passed directly to the reabsorber without ever passing through the stripper.

10. The method as claimed in claim 4 wherein the dilute alkaline solution is 1-15% alkaline hydroxide.

* * * * *